(12) United States Patent
DeRosier

(10) Patent No.: US 8,338,187 B2
(45) Date of Patent: Dec. 25, 2012

(54) METHODS AND SYSTEMS FOR CONTROLLING LIQUIDS IN MULTIPLEX ASSAYS

(75) Inventor: Chad F. DeRosier, San Diego, CA (US)

(73) Assignee: Illumina, Inc., San Diego, CA (US)

(*) Notice: Subject to any disclaimer, the term of this patent is extended or adjusted under 35 U.S.C. 154(b) by 8 days.

(21) Appl. No.: 13/143,027

(22) PCT Filed: Feb. 23, 2010

(86) PCT No.: PCT/US2010/025071
§ 371 (c)(1),
(2), (4) Date: Jun. 30, 2011

(87) PCT Pub. No.: WO2010/104672
PCT Pub. Date: Sep. 16, 2010

(65) Prior Publication Data
US 2011/0269641 A1  Nov. 3, 2011

Related U.S. Application Data

(60) Provisional application No. 61/160,174, filed on Mar. 13, 2009.

(51) Int. Cl.
*G01N 1/10* (2006.01)
*B01L 3/00* (2006.01)

(52) U.S. Cl. ........ 436/180; 422/407; 422/501; 422/502; 422/503; 422/551; 422/552; 422/553

(58) Field of Classification Search ........... 422/407, 422/500, 502–504, 550–553, 559; 436/180
See application file for complete search history.

(56) References Cited

U.S. PATENT DOCUMENTS

| | | | |
|---|---|---|---|
| 4,294,931 A * | 10/1981 | Levin et al. | 435/288.5 |
| 6,086,825 A | 7/2000 | Sundberg et al. | |
| 6,143,250 A * | 11/2000 | Tajima | 422/553 |
| 6,284,113 B1 | 9/2001 | Bjornson et al. | |
| 6,485,690 B1 | 11/2002 | Pfost et al. | |
| 6,500,390 B1 * | 12/2002 | Boulton et al. | 506/43 |
| 6,657,169 B2 * | 12/2003 | Brown | 219/476 |

(Continued)

OTHER PUBLICATIONS

PCT Notification of International Search Report and Written Opinion of PCT/US2010/025071 (11 pgs.).

*Primary Examiner* — Brian R Gordon
(74) *Attorney, Agent, or Firm* — The Small Patent Law Group, LLC; Dean Small; Jason P. Gross

(57) ABSTRACT

Methods and systems for venting a well that receives a liquid. The method includes providing a microplate including a well that has a cavity with an open inlet and a closed end. The cavity extends between the open inlet and the closed end. The cavity is defined by a wall surface having a cross-sectional contour that includes at least one continuous section and at least one discontinuity section. The method also includes depositing a liquid into the open inlet of the well. The liquid enters the cavity and flows toward the closed end to at least partially fill the well. The liquid flows along the continuous section of the wall surface and remains separated from the discontinuity section of the wall surface, thereby maintaining a gas exhaust path along a spacing between the liquid and the discontinuity section as the liquid flows toward the closed end.

28 Claims, 11 Drawing Sheets

U.S. PATENT DOCUMENTS 7,407,630 B2     8/2008  Reed et al.
7,662,345 B2 *   2/2010  Kawahara et al. ............ 422/504
2002/0172621 A1* 11/2002 Barbera-Guillem .......... 422/100
2007/0217955 A1* 9/2007  Kawahara et al. .............. 422/99
2010/0190197 A1* 7/2010  Martin et al. ................... 435/29

* cited by examiner

METHODS AND SYSTEMS FOR CONTROLLING LIQUIDS IN MULTIPLEX ASSAYS

CROSS-REFERENCE TO RELATED APPLICATIONS

This application claims the benefit of U.S. Provisional Application No. 61/160,174, filed on Mar. 13, 2009, which is incorporated by reference in the entirety.

BACKGROUND OF THE INVENTION

Embodiments of the present invention relate generally to methods and systems for biological and chemical analysis, and more specifically to fluidic methods and systems for preparing and using microarrays in biological and chemical analysis.

Microarrays may be used in various types of biological and chemical analysis, such as in genomic research, drug screening, or screening for infectious diseases. Microarrays generally include sample regions of known biomolecules, also referred to as probes, that are immobilized onto a surface of a substrate, such as a slide. The probes may be, for example, polynucleotides, proteins, other chemical compounds, or tissues. The sample regions are arranged on the surface (e.g., rows and columns) so that each sample region will have a known location or address on the surface of the substrate. The sample regions are then exposed to a target solution containing biomolecules, also called targets, to determine if the targets bind to any of the probes.

For example, in one conventional system, the sample regions are located in an array at the bottom of a well in a microplate. A loading station that has several pipettes or syringes is used to deliver a drop of a target solution into each of the wells so that the drop is placed onto the corresponding sample region. The biomolecules of the target solution are labeled so that the target biomolecules have an optically detectable quality (e.g, fluorescence). When exposed to the probes of the sample regions, the target biomolecules selectively bind (e.g., through hybridization) with certain probes. To facilitate the binding process, the microarray may be placed within an oven where the microarray undergoes a predetermined thermal cycle. After the binding reaction is completed, the microarray is washed to remove any undesired residue and may be then exposed to other solutions (e.g., another target solution, staining solutions). When ready, the microarray is scanned to determine which probes have a binding affinity for the target biomolecules. For example, if the target biomolecules were fluorescently labeled, a reader could scan the microarray to detect any fluorescence. The level of fluorescence emitting from each sample region (or from particular portions of each sample region) indicates a binding affinity that the probes and target biomolecules have for each other. The observed fluorescent pattern provides information on the sequence or structure of the target biomolecules.

However, the process for providing a solution to the sample regions may have certain limitations. For example, when the drop of the target solution is placed onto the corresponding sample region, small bubbles may form within the drop on the surface of the substrate. If the bubbles are located on the sample region, the bubbles may prevent the biomolecules of the target solution from interacting with the probes of the sample region. When the sample region is subsequently scanned, those portions of the sample region where the bubbles prevented the interaction between the biomolecules and probes may not indicate the correct binding affinity. Some methods have been used for removing the bubbles from the target solution when the target solution has been deposited onto the sample region. For example, each well of the microplate may include a separate outlet or channel for removing gases or bubbles formed within the solution. However, using a separate channel to remove the bubbles adds complexity to the system and may also reduce the available space on the microarray.

Another limitation is that conventional loading stations typically use automated or robotic devices for delivering the target solution onto the sample regions. The loading stations are programmed to draw solution from a source or reservoir (e.g., with pipettes or syringes) and automatically deliver the solution to the wells of the microplate. However, the conventional loading stations are complex systems that may be very expensive and require maintenance that is also costly. Furthermore, the loading stations may be limited in the types of microarrays (e.g., size and density of sample regions) that are compatible with the loading stations.

Accordingly, there is a need for improved systems, devices, and methods for reducing gases within a solution. There is also a need for improved systems, devices, and methods for conveying the target solution to the sample region in an efficient manner. Furthermore, there is a need for improved methods and systems for fluidic control during biological or chemical assays.

BRIEF DESCRIPTION OF THE INVENTION

In accordance with one embodiment, a method for venting a well into which a liquid enters is provided. The method includes providing a microplate having a well that includes a cavity with an open inlet and a closed end. The cavity extends between the open inlet and the closed end. The cavity is defined by a wall surface having a cross-sectional contour that includes at least one continuous section and at least one discontinuity section. The method also includes depositing a liquid into the open inlet of the well. The liquid enters the cavity and flows toward the closed end to at least partially fill the well. The liquid flows along the continuous section of the wall surface and remains separated from the discontinuity section of the wall surface, thereby maintaining a gas exhaust path along a spacing between the liquid and the discontinuity section as the liquid flows toward the closed end to permit discharge of gas from the closed end of the well.

In a further embodiment, a microplate that is configured to facilitate venting a well that receives a liquid is provided. The microplate includes a well having a cavity with an open inlet and a closed end. The cavity extends between the open inlet and the closed end and is defined by a wall surface that has a cross-sectional contour. The cross-sectional contour has at least one continuous section and at least one discontinuity section. The liquid partially fills the well when deposited therein. The cross-sectional contour is shaped to define a spacing between the discontinuity section and the liquid. The spacing providing a gas exhaust path to permit discharge of gas from the closed end.

In yet another embodiment, a gasket that is configured to be mounted onto a substrate is provided. The gasket includes a body that is configured to be mounted to a surface of the substrate. The body has a pair of sides separated by a thickness. The gasket also includes a passage that extends between the pair of sides through the body between an open inlet and an open outlet. The passage is defined by a wall surface that has a cross-sectional contour that includes at least one continuous section and at least one discontinuity section. The passage forms a well with the surface of the substrate when the body is mounted thereon. The liquid partially fills the well when deposited therein. The cross-sectional contour is shaped to define a spacing between the discontinuity section and the liquid. The spacing provides a gas exhaust path to permit discharge of gas from the well that the liquid enters.

In a further embodiment, a fluidic device for conveying liquid to a well of a microplate is provided. The device includes a support structure that is configured to be mounted along the microplate and a microfluidic tube that is coupled to the support structure. The tube has an inlet, an outlet, and an open-sided channel that extends longitudinally therebetween. The tube has a cross-section that includes an interior contour with a gap therein. The gap extends at least partially along a length of the tube. The tube is configured to convey liquid to the well of the microplate when the tube is held in a dispensing orientation.

In yet another embodiment, a method of conveying liquid from a source well of a microplate is provided. The method includes inserting a microfluidic tube into the source well of the microplate. The tube has an inlet, an outlet, and an open-sided channel that extends longitudinally therebetween. The tube has a cross-section that includes an interior contour with a gap therein. The gap extends at least partially along a length of the tube. The method also includes orienting the tube with respect to a gravitational force direction into a dispensing orientation and loading the liquid from the source well into the tube. The liquid is exposed along the open-sided channel as the liquid flows down the tube.

In a further embodiment, a fluidic system configured to convey liquid between wells is provided. The system includes a first microplate that has a source well and a second microplate that has a reaction well. The system also includes a support structure that is configured to be mounted along at least one of the first and second microplates. Also, the system includes a microfluidic tube that is coupled to the support structure. The tube has an inlet, an outlet, and an open-sided channel that extends longitudinally therebetween. The tube has a cross-section that includes an interior contour with a gap therein. The gap extends at least partially along a length of the tube. The tube is configured to convey liquid to the well of the microplate when the tube is held in a dispensing orientation. The outlet of the tube is held in the reaction well of the second microplate and the inlet of the tube is inserted into the source well of the first microplate to convey liquid from the source well to the reaction well.

DETAILED DESCRIPTION OF THE INVENTION

Figure 1:
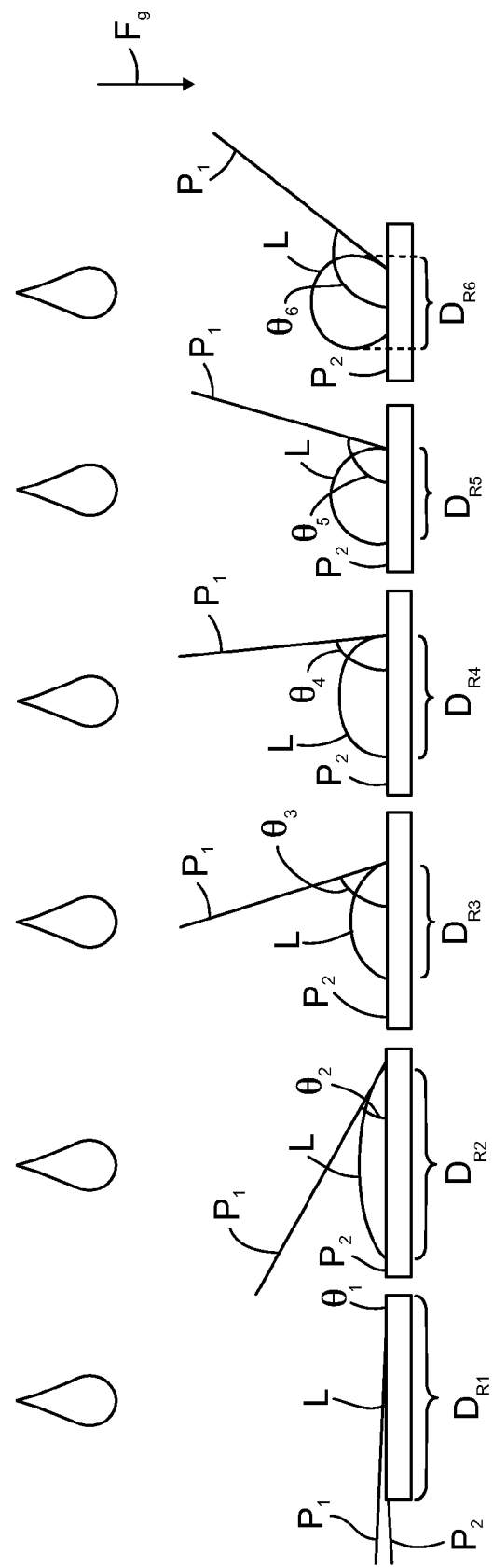
FIG. 1 illustrates a series of drops of liquid on different surfaces.

Embodiments described herein include various methods, devices, and systems that use forces experienced by a liquid within a fluidic system to control flow of the liquid and/or to vent or discharge gases from a chamber into which the liquid enters. For example, in order to control the flow of the liquid and to deposit the liquid on a desired location, various embodiments may use gravitational force, cohesive forces, and/or adhesive forces to control the flow of liquid from a source or reservoir to a sample region. Various embodiments may also use gravitational force, cohesive forces, capillary forces, surface tension and/or adhesive forces to contain a liquid within a confined space and vent gases from the confined space.

In some embodiments, the flow and/or venting of the space where the liquid is located is facilitated by or is solely accomplished by passive methods. As used herein, controlling the flow of liquid or the venting of gases "passively" means utilizing energy that is innate to the system or potential energy of the system to effect flow or venting. Accordingly, passive control of liquid flow or venting need not utilize kinetic energy produced outside of the system, for example, being carried out without using a pumping system to transfer the liquid between locations and/or to remove gases from the location. For example, some embodiments may transfer liquid from one location to another and vent gases without using syringes or pipettes to hold and relocate the liquid or separate channels to remove the gases. However, the pumping systems may, in some embodiments, include mechanical pumps or micropumps and electroosmotic pumps. As another example of a passive method, the flow of liquid from a source well may be initiated by positive displacement, but the flow is maintained and controlled by gravitational, cohesive, and/or adhesive forces. However, other embodiments are not limited to passive means, and the methods, devices, and systems described herein may be used in conjunction with pumping systems that actively control the flow of liquid and/or gases.

As used herein, a "sample region" includes any portion of a surface of the substrate where analytes of interest, such as biomolecules, are located. The sample region may also be referred to as a feature. The biomolecules may be immobilized onto the surface of the substrate in the sample region. In some embodiments, each sample region has a plurality of smaller sample regions, or sub-features, that may also be arranged into an array (or sub-array) on the surface of the substrate. As used herein, "biomolecules," may be naturally occurring or synthetically made and include polynucleotides, oligonucleotides, proteins, enzymes, polypeptides, antibodies, antigens, ligands, receptors, polysaccharide, carbohydrate, or any other chemical compound desired to be studied or analyzed. Other analytes that are useful include small molecules, whether naturally occurring or synthetic and whether biologically active or inert. Cells, tissues, organisms and the like are also useful analytes. The analytes may also be referred to as "targets" or "probes." The biomolecules within a single sample region may be different or, alternatively, each sample region may include biomolecules having a common chemical structure. Although several embodiments are exemplified herein with respect to biomolecules, it will be understood that other analytes can be used similarly.

As used herein, a "substrate" includes any structure that may hold the deposited amount of liquid. For example, the substrate may be a multi-well plate or a slide with a planar surface. The substrate may include an array of sample regions or may include only one sample region that, for example, covers most of or the entire surface of the substrate. In addition, the sample regions may be arranged in a predetermined manner such that each sample region is addressable (i.e., the biomolecules in the sample region may be identified based upon the location of the sample region on the surface). Each sub-array within the corresponding sample region may also be addressable. Furthermore, the substrate may have a planar surface or may include cavities, wells, grooves, and the like.

As used herein, a "microarray" generally includes a substrate that has a plurality of sample regions thereon for multiplex analysis. A microarray may be a microplate having a plurality of wells (e.g., 96) where the sample regions are located. Also, a microarray may be a chip having a plurality of sample regions thereon where each chip is positioned within a well of a microplate or a larger microarray. As such, each well may have a microarray held therein.

A microarray used in a method described herein can have a plurality of features including, for example, at least about 100, 500, $1 \times 10^3$, $5 \times 10^3$, $1 \times 10^4$, $1 \times 10^5$, $1 \times 10^6$ or more features. The density of features on an array can be, at least about 100, 500, $1 \times 10^3$, $5 \times 10^3$, $1 \times 10^4$, $1 \times 10^5$, $1 \times 10^6$ or more features per square centimeter. In particular embodiments, a bead-based array can be used in which microspheres or beads are arrayed or otherwise spatially distinguished. Exemplary bead-based arrays that can be used in the invention include, without limitation, those in which beads are associated with a solid support such as those described in U.S. Pat. No. 6,355,431 B1; US 2002/0102578; and WO 00/63437, each of which is incorporated herein by reference. Beads can be located at discrete locations, such as wells, on a solid-phase support, whereby each location accommodates a single bead. Alternatively, discrete locations where beads reside can each include a plurality of beads as described, for example, in US 2004/0263923, US 2004/0233485, US 2004/0132205, or US 2004/0125424, each of which is incorporated herein by reference. The beads can be encoded by any of a variety of properties known in the art including, without limitation, nucleic acid sequences, color, diffraction grating patterns and the like.

Any of a variety of arrays known in the art can be used in the present invention. For example, arrays that are useful in the invention can be non-bead-based. Particularly useful arrays are Affymetrix™ GeneChip® arrays, examples of which are described, for example, in U.S. Pat. No. 7,087,732 or U.S. Pat. No. 6,747,143, each of which is incorporated herein by reference. A spotted array can also be used in a method of the invention. An exemplary spotted array is a CodeLink™ Array previously available from Amersham Biosciences. Another array that is useful in the invention is one manufactured using inkjet printing methods such as SurePrint™ Technology available from Agilent Technologies. Arrays used in various sequencing platforms are also useful such as those used for Solexa (now Illumina, Inc., San Diego, USA) sequencing technology as described, for example, in US 2007/0015200; US 2004/0106110; US 2003/0064398 or US 2003/0022207; those used in 454 Biosciences (now Roche Diagnostics, Basel, Switzerland)) sequencing technology such as those described in US 2006/0040297 or U.S. Pat. No. 7,211,390; or those used in Applied Biosystems (now Life Technologies, San Diego, USA) sequencing methods such as those described in US 2006/0024681 each of which is incorporated herein by reference.

A "liquid," as used herein, is a substance that is relatively incompressible and has a capacity to flow and to conform to a shape of a container or a channel that holds the substance. The liquid may be aqueous based and include polar molecules exhibiting surface tension that holds the liquid together. The liquid may also comprise non-polar molecules, such as in an oil-based or non-aqueous substance. A "microfluidic tube" includes a channel having dimensions in which the surface tension and cohesive forces of the liquid and the adhesive forces between the liquid and the surfaces of the channel have a significant effect on the flow of the liquid. For example, a channel of the microfluidic tube may have a diameter that is less than 1 mm or, more specifically, less than 0.6 mm, 0.5 mm, 0.4 mm, 0.3 mm, 0.2 mm, 0.1 mm or 0.05 mm or less. Alternatively or additionally, the tube can have a maximum diameter of at most 0.1 mm, 0.2 mm, 0.3 mm, 0.4 mm, 0.5 mm, 0.6 mm or 1 mm or more. As set forth elsewhere herein, the tube need not have a circular cross section. Nevertheless, the cross section of the tubes can have an area that is equivalent to the area of the circular cross sections set forth above. Also, a path taken by the liquid along the microfluidic channel may be substantially linear or redirected in many directions. The liquid may be deposited directly onto a desired location from the microfluidic channel or the liquid may be deposited elsewhere on the surface and moved to the desired location. For example, a drop of liquid may be deposited onto a wall surface within a well and gravity may pull the drop along the wall surface and onto a bottom surface within the well.

In some embodiments, an approximate or precise amount of the liquid (e.g., a drop or an aliquot) may be placed onto the surface of the substrate covering the sample region. The drop may be partially contained, for example, within a well that has a limited volume or the drop may rest upon a surface without being compressed or shaped by walls. The liquid may form a bead on the surface or the liquid may spread along the surface through wetting and/or by being compressed into the surface.

FIG. 1 illustrates a series of drops of liquid L on different surfaces. As discussed above, embodiments described herein utilize the forces experienced by the liquid L to control the flow of the liquid L and venting of gas. These forces include cohesive forces (i.e., attractive forces between like molecules of the liquid L) and adhesive forces (i.e., attractive forces between molecules of the liquid L and a solid surface or vapor that surrounds the liquid). Cohesive and adhesive forces arise from the interaction of atoms and molecules that are located along, for example, a liquid-vapor interface and a liquid-solid interface. Another force that affects the flow of liquid in embodiments describe herein is gravity or the gravitational force $F_g$.

Depending upon the nature of the liquid L and the solid surface, FIG. 1 shows various resting diameters $D_{R1}$-$D_{R6}$ and contact angles $\theta_1$-$\theta_6$. A resting diameter $D_R$ is the diameter of the drop of liquid L on a corresponding planar solid surface where the drop of the liquid L is not compressed or contained by walls. The resting diameter $D_R$ is measured parallel to the planar solid surface. A contact angle $\theta$ is the angle formed by the intersection of two planes ($P_1$ and $P_2$) tangent to the liquid L and the corresponding solid surface. When the contact angle $\theta$ is greater than 90°, the resting diameter $D_R$ remains substantially the same (e.g., $D_{R5}$ and $D_{R6}$ are about equal). The contact angle $\theta$ indicates a wetting ability of the liquid to the surface. Wetting is a liquid's ability to spread along a solid surface. The wetting of a solid surface by a liquid is controlled by the intermolecular interactions of molecules along an interface between the two phases. If the adhesive forces are relatively greater than the cohesive forces, the wetting of the liquid to the surface is greater (i.e., the contact angle θ will be small as shown with contact angles $\theta_1$ and $\theta_2$ in FIG. 1). If the cohesive forces are relatively greater than the adhesive forces, the wetting of the liquid to the surface is smaller (i.e., the contact angle θ will be large as shown with contact angles $\theta_5$ and $\theta_6$).

Surface tension in a liquid is caused by the cohesive forces of the liquid and, as such, can have an affect on the contact angle θ. As the surface tension increases, an ability of the liquid to reduce its surface area (i.e., bead up) also increases. Surfaces of solids, however, may be characterized as having a surface energy. As the surface energy of a solid increases, the ability of the solid to interact with the liquid also increases (i.e., the contact angle θ decreases). As an example, when a liquid of low surface tension is placed on a solid of high surface energy, the liquid spreads across the surface and has a small contact angle θ. If a liquid has a high surface tension and is placed on a surface of low surface energy, the liquid may form a bead on the surface and have a high contact angle θ. As will be discussed in greater detail below, the flow of the liquid L and the venting of gases may be determined by the surface tension of the liquid and the surface energy of the solid surface.

In embodiments utilizing aqueous or polar liquids, the interaction between the liquid L and the solid surface can be characterized as hydrophobic or hydrophilic. As used herein, a solid surface is hydrophobic if it repels an aqueous or polar liquid. For example, the contact angle θ between the aqueous or polar liquid L and the hydrophobic surface of the solid is typically greater than 90 degrees. A surface is hydrophilic if it is attracted to an aqueous or polar liquid L. For example, the contact angle θ between the aqueous or polar liquid L and the hydrophilic surface of the solid will typically be less than 90 degrees.

In other embodiments, a non-polar liquid, such as alkanes, oils, and fats may be used as the liquid L. Non-polar liquids may be attracted to a surface that has a hydrophobic interaction with aqueous or polar liquids. Likewise, non-polar liquids are not attracted to a surface that has a hydrophilic interaction with aqueous or polar liquids. As such, hydrophobic and hydrophilic surfaces may be used with embodiments described herein to control the flow of a non-polar liquid and to vent chambers having the non-polar liquid therein.

Embodiments described herein utilize the contact angle or the wetting of a liquid and a shape of a solid surface to control the flow of the liquid L and to vent gases from a confined space that the liquid L enters. Other factors may affect the contact angle θ or the wetting of a liquid to a solid. For example, a purity of the liquid L or whether a surfactant is used may affect the surface tension of the liquid and the molecular interactions along the solid-liquid interface. A purity of the solid or whether a coating is placed on the solid surface may affect the surface energy of a solid. Also, temperature of the environment, a composition of the surrounding air, and the roughness or smoothness of the surface may all affect the interactions between the liquid L and the solid surface.

The concepts discussed briefly above are discussed in greater detail in *Surfaces, Interfaces, and Colloids: Principles and Applications, Second Edition*, Drew Meyers, 1999, John Wiley & Sons, Inc. and in *Contact Angle, Wettability, and Adhesion*, edited by Robert F. Gould (1964), both of which are hereby incorporated by reference.

Figure 2:
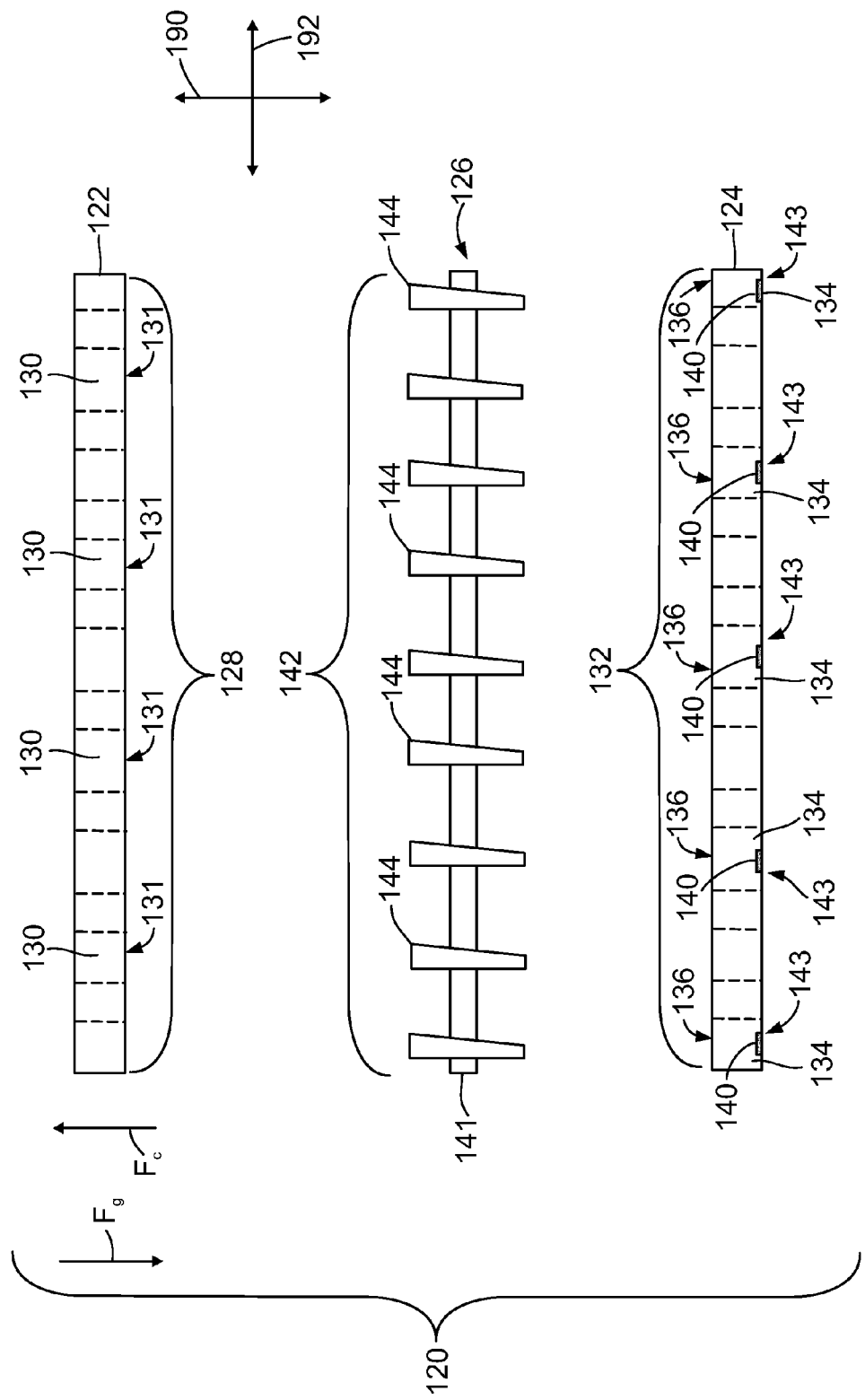
FIG. 2 is an exploded side view of a fluidic system formed in accordance with one embodiment.

FIG. 2 is an exploded view of a fluidic system 120 formed in accordance with one embodiment. The fluidic system 120 is configured to convey liquid (not shown) between microplates 122 and 124 through a fluidic device 126. The microplate 122 may include an array 128 of source wells 130 where each source well 130 contains an amount of the liquid. The source wells 130 include openings 131 for accessing the source wells 130. The microplate 124 may include an array 132 of reaction wells 134 that also have an opening 136. Each reaction well 134 may include a sample region 140, such as a microarray on a chip, located at a bottom 143 of the corresponding reaction well 134. The microplates 122 and 124 may be, for example, multi-well plates. In another embodiment, the microplate 124 may comprise a substrate and a gasket mounted to the substrate.

As shown, the microplate 122 is in an inverted position such that the openings 131 of the source wells 130 face substantially in a direction with a gravitational force direction $F_g$ (i.e., a vertical direction along an axis 190). The source wells 130 may be sized and shaped such that the liquid remains in the corresponding source wells 130 due to capillary forces $F_c$ when the microplate 122 is in the inverted position. Capillary forces $F_c$ include the adhesive and cohesive forces experienced by the liquid within the source well 130. In such positions, the capillary forces $F_c$ created by the liquid and the walls of the source wells 130 are greater than the gravitational force $F_g$. The volume and composition of the liquid can be selected such that cohesive and adhesive forces are sufficient to retain the liquid in the well.

The fluidic device 126 has a support structure 141 having an array 142 of microfluidic tubes 144 coupled thereto. The fluidic device 126 is configured to be mounted to either or both of the microplates 122 and 124. The support structure 141 may be substantially planar and extend along a horizontal axis 192 when the fluidic device 126 is mounted to one of the microplates 122 and 124. Each tube 144 may have a common orientation with respect to the other tubes 144. As shown, the tubes 144 may extend substantially along the vertical axis 190 or substantially along the direction of the gravitational force Fg. The arrays 128, 132, and 142 may be matching such that, when the fluidic device 126 is mounted to either of the microplates 122 and 124, the microfluidic tubes 144 may be inserted into the corresponding wells.

By way of example, in order to convey liquid between the source wells 130 and corresponding reaction wells 134, the fluidic device 126 may be mounted to the microplate 124. A portion of each tube 144 may be inserted through the opening 136 of a corresponding reaction well 134. The tube 144 may contact the bottom 143 of the reaction well 134 near the sample region 140 or may be suspended within a volume of the reaction well 134. The microplate 122 may then be lowered onto the fluidic device 126 such that a portion of each tube 144 is inserted into a corresponding source well 130. When the portion of the tube 144 advances through the opening 131 of the source well 130, the tube 144 may displace a portion of a volume of the liquid therein forcing the liquid into the tube 144. Each tube 144 is configured to allow the liquid within the corresponding source well 130 to be drawn therethrough and into the corresponding reaction well 134. The tube 144 may be configured to locate a drop or a liquid aliquot onto the bottom 143 of the reaction well 134 and cover the sample region 140. Alternatively, the tube 144 may be shaped to locate the liquid onto a sidewall of the reaction well 134 or another desired location.

The fluidic device 126 may have mating features that engage or otherwise fasten the fluidic device 126 to a plate of source wells, a plate of reaction wells or both. For example, a post (not shown) projecting from the fluidic device 126 may form an interference fit with a corresponding cavity (not shown) in the plate of source wells or the plate of reaction wells. Furthermore, other devices, such as tabs or a clamp, may be used to hold the fluidic device 126 onto the plate of source wells or the plate of reaction wells. As such the mating features can provide alignment of tubes to wells.

Figure 3:
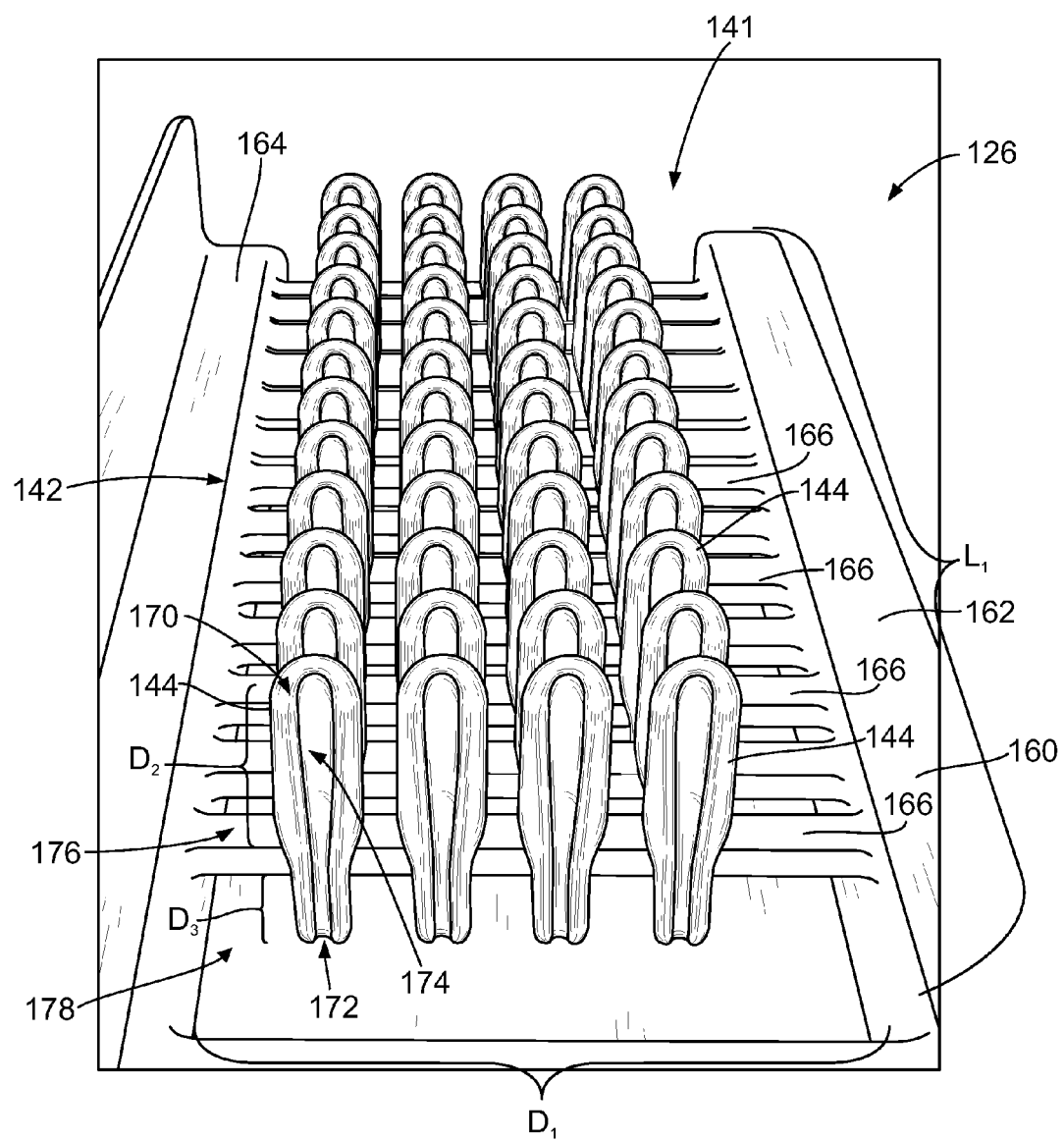
FIG. 3 is a perspective view of a fluidic device in accordance with one embodiment that may be used with the fluidic system shown in FIG. 2.

FIG. 3 is a perspective view of the fluidic device 126. The support structure 141 may have a generally planar or rectangular body 160 that is configured to hold the array 142 of the tubes 144 in a common orientation. The body 160 may include a pair of spaced apart beams 162 and 164 that extend along a common plane and may be parallel to each other. As shown, the beams 162 and 164 have a length $L_1$ and are separated from each other by a distance $D_1$. The beams 162 and 164 may be joined to each other by one or more bridge members 166 that extend across the distance $D_1$ and provide support and stability to the fluidic device 126. Each tube 144 may be coupled to the support structure 141 via a corresponding bridge member 166. As shown, the array 142 of the tubes 144 may be arranged in a plurality of rows and columns in a grid-like format. Alternatively, the tubes 144 may have other arrangements. In some embodiments, the fluidic device 126 may be integrally formed such that the support structure 141 and the tubes 144 are made altogether through, e.g., an injection molding process.

Alternatively, the tubes 144 may be separately inserted into holes within the corresponding bridge member 166 or form a snap-fit with the bridge member 166. In another alternative embodiment, individual bridge members 166 may be integrally formed with a series of tubes 144. Each bridge member 166 in such embodiments may be removably coupled (e.g., through interference fitting) to a pair of beams to form the fluidic device 126. Thus, the array 142 of tubes 144 may be reconfigurable in some embodiments.

Each tube 144 may have an inlet 170, an outlet 172, and an open-sided channel 174 extending therebetween. The tube 144 may also have an inlet portion 176 that is sized and shaped to be inserted into the source well 130 (FIG. 2) and an outlet portion 178 that is sized and shaped to be inserted into the reaction well 134 (FIG. 2). The inlet and outlet portions 176 and 178 may project a distance $D_2$ and $D_3$, respectively, from the corresponding bridge member 166. The distances $D_2$ and $D_3$ are configured along with other dimensions of the tubes 144, source wells 130, and reaction wells 134 in order to facilitate conveying the liquid from the source well 130 to the reaction well 134.

Figure 4:
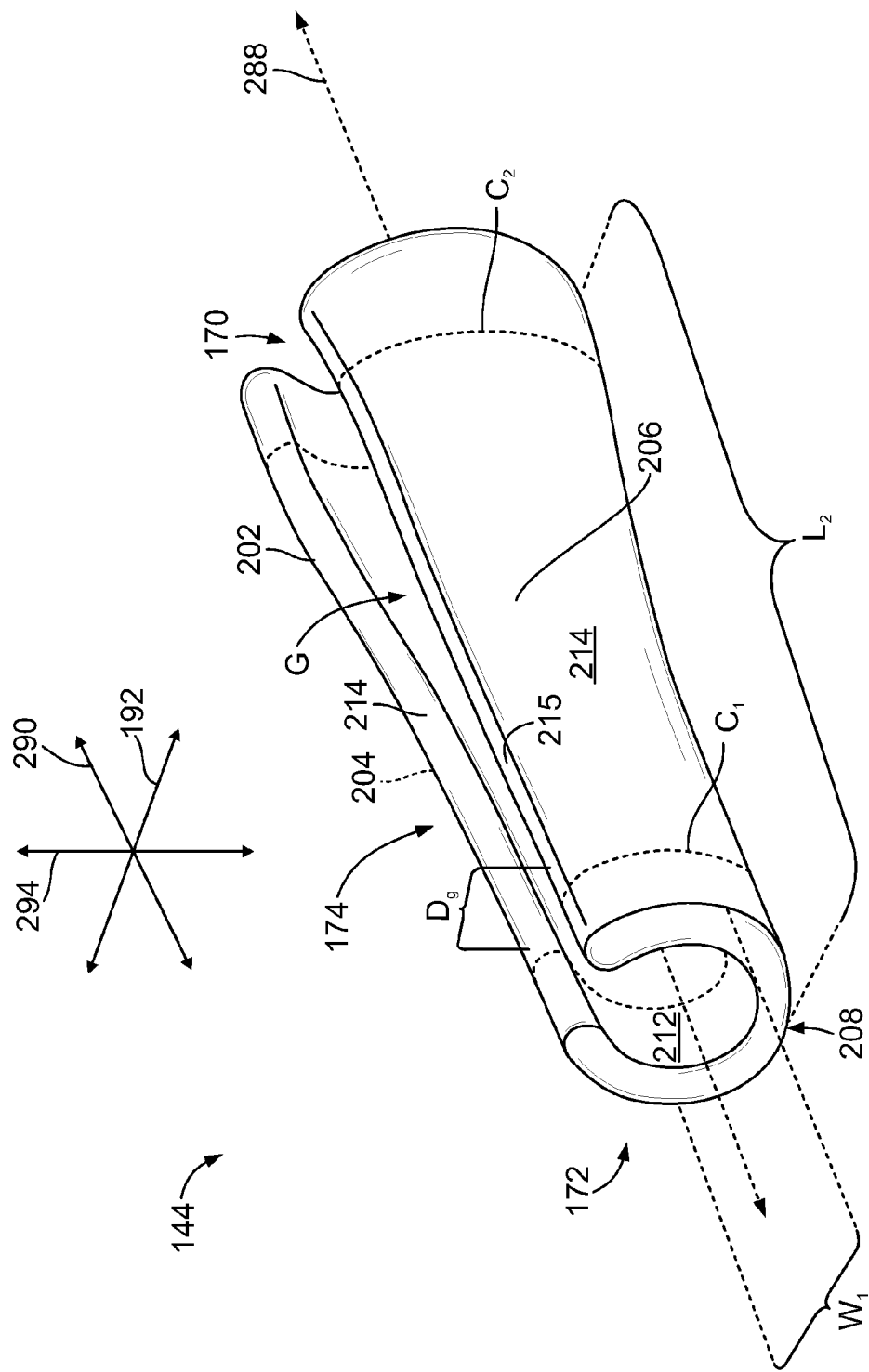
FIG. 4 is a perspective view of a microfluidic tube that may be used with the fluidic device shown in FIG. 3.

FIG. 4 is a perspective view of the tube 144. The tube 144 is shown in relation to axes 290, 292, and 294. The tube 144 includes a body 202 that has the inlet 170, the outlet 172, and the open-sided channel 174 extending therebetween along a central longitudinal axis 288 of the body. The body 202 has a length $L_2$ that extends between the inlet 170 and the outlet 172 along the longitudinal axis 288. As the body 202 extends lengthwise along the longitudinal axis 288 a cross-sectional shape of the body may vary. For example, the body 202 may have a width $W_1$ that varies as the body 202 extends along the length $L_2$ of the body. Although the body 202 in FIG. 4 is substantially linear with respect to the longitudinal axis 288, the body 202 is not required to be straight. For example, the body 202 may curve or shift in order to deposit the liquid at a desired location within the reaction well 134 (FIG. 2).

The body 202 of the tube 144 includes a pair of opposing arms 204 and 206 that surround the longitudinal axis 288 and join each other at a center portion 208 of the body 202. The body 202 has an inner surface 212 and an exterior surface 214. The inner surface 212 defines the channel 174. The channel 174 is open-sided such that when the liquid flows down the channel 174, the liquid is exposed to ambient or surrounding air. As shown, a gap G extends along the length $L_2$ of the body 202 separating the arms 204 and 206 from each other. More specifically, the arms 204 and 206 may have corresponding end portions 214 and 215. When the gap G separates the arms 204 and 206, the end portions 214 and 215 of each arm 204 and 206, respectively, are spaced apart from each other by a gap distance $D_g$. The gap G may extend the entire length $L_2$ from the inlet 170 to the outlet 172 as shown in FIG. 4. However, in other embodiments, the gap G may extend along one or more portions of the body 202 within intervening portions that do not have a gap.

As shown in FIG. 4, the outlet 172 has a substantially planar front end with respect to a plane that is formed by the axes 294 and 290 and that is transverse to the longitudinal axis 288. However, in alternative embodiments, the outlet 172 may be shaped as desired. For example, the outlet 172 may be shaped to facilitate the tube 144 locating the reaction well 134 that the tube 144 is being inserted into. More specifically, the outlet 172 may form a point or a projection that has a cross-sectional area smaller than a cross-sectional area of the well. Likewise, the inlet 170 may be sized and shaped to facilitate locating the source well when the tube 144 is moved thereto.

Furthermore, the channel 174 has a cross-sectional area at the inlet 170 and a cross-sectional area at the outlet 172. In a particular embodiment, the cross-sectional areas at the inlet 170 and at the outlet 172 are different. For example, the cross-sectional area of the channel 174 at the inlet 170 may be greater than the cross-sectional area of the outlet 172.

Figure 5:
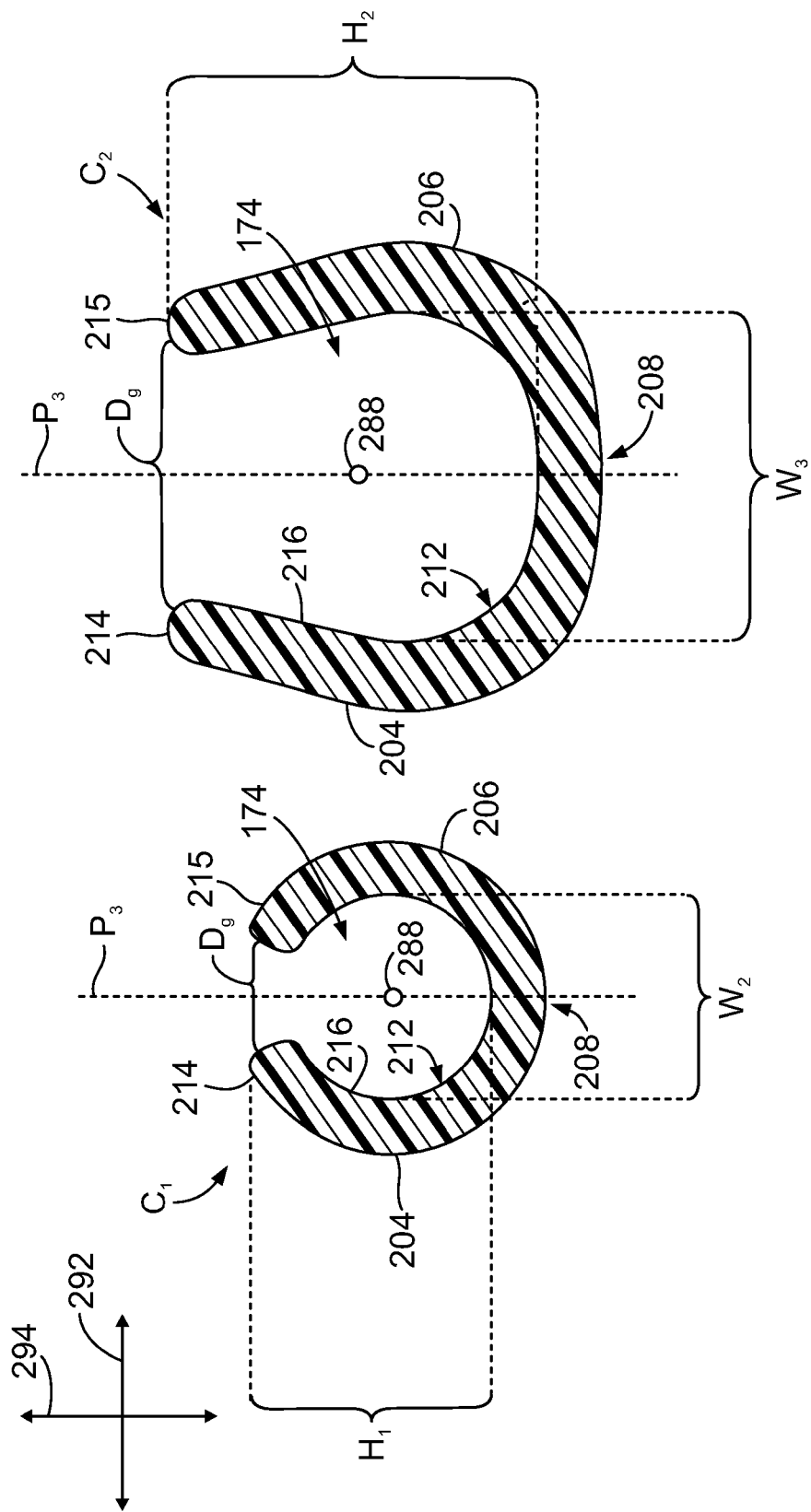
FIG. 5 illustrates a pair of cross-sections $C_1$ and $C_2$ of the tube shown in FIG. 3.

FIG. 5 shows cross-sections $C_1$ and $C_2$ of the tube 144 taken transverse to the longitudinal axis 288 in FIG. 4. The cross-section $C_1$ is from the outlet portion 178 (FIG. 3) and the cross-section $C_2$ is from the inlet portion 176 (FIG. 3). The cross-sections $C_1$ and $C_2$ are described with reference to a plane $P_3$ that extends through the longitudinal axis 288 and the center portion 208 and is perpendicular to a plane formed by the axes 292 and 294. As shown, the plane $P_3$ may bisect the body 202 such that the arms 204 and 206 are symmetrical about the plane $P_3$.

The cross-sections $C_1$ and $C_2$ illustrate an interior contour 216 of the channel 174 that is defined by the inner surface 212. The interior contour 216 includes the gap G (FIG. 4) that separates the opposing arms 204 and 206 by a gap distance $D_g$. The interior contour 216 may be sized and shaped at different portions along the channel 174 to facilitate controlling the flow of liquid (not shown). For example, the inner surface 212 may curve about the longitudinal axis 288 such that the interior contour 216 is substantially C-shaped or U-shaped. The cross-section $C_2$ may be sized and shaped to be inserted into and receive the liquid from the source well 130 and allow the liquid to be pulled by the gravitational force $F_g$ (FIG. 2) through the channel 174. The cross-section $C_1$ may be sized and shaped to deposit the liquid onto a desired location within the reaction well 134 (FIG. 2).

By way of example, the channel 174 has maximum widths $W_2$ and $W_3$ at cross-sections $C_1$ and $C_2$, respectively, that extend between the arms 204 and 206 along the axis 292. The cross-section $C_1$ also has a maximum height $H_1$ that extends along the axis 294 from the center portion 208 to proximate the end portions 214 and 215. Likewise, the cross-section $C_2$ has a maximum height $H_2$ that extends along the axis 294 from the center portion 208 to a position proximate to the end portions 214 and 215. The ratio of the maximum height to the maximum width for a cross-section can be any of a variety of ratios that support movement of a liquid. In particular embodiments, the ratio of maximum height to maximum width can be at least 0.5 to 1, at least 1 to 1, at least 1.5 to 1 at least 5 to 1 or the ratio can be higher. Alternatively or additionally, the ratio of maximum height to maximum width can be at most 10 to 1, at most 5 to 1, at most 1.5 to 1 or at most 1 to 1. Such ratios are particularly useful for tubes having a C-shaped or U-shaped cross-section, examples of which are shown in FIGS. 5 and 6.

Accordingly, the cross-sections $C_1$ and $C_2$ may have different dimensions to control the flow of the liquid therethrough. As shown in FIG. 5, the width $W_3$ can be at least greater than the width $W_2$. The gap distance $D_g$ at the cross-section $C_2$ is greater than the gap distance $D_g$ at the cross-section $C_1$. The height $H_2$ is greater than the height $H_1$. As such, a cross-sectional area of the channel 174 within the inlet portion 176 is greater than a cross-sectional area of the channel 174 at the outlet portion 178. Furthermore, the shapes of the interior contour 216 at cross-section $C_1$ and at cross-section $C_2$ may also be different. As shown, the interior contour 216 may be substantially C-shaped at the cross-section $C_1$, but may be substantially U-shaped at the cross-section $C_2$.

In some embodiments, the open-sided channel 174 may reduce the capillary forces $F_c$ (FIG. 2) that might impede or prevent the liquid from flowing therethrough. Also, the dimensions of the inlet portion 176 provide a larger cross-sectional area for the liquid to flow therethrough as compared to the outlet portion 178. In such embodiments, the capillary forces $F_c$ are reduced along the inlet portion 176 and the flow of liquid may be faster therethrough than the flow of the liquid through the outlet portion 178.

However, the above description of the shapes and dimensions of the interior contour 216 is only one example and the cross-sections of interior contour 216 may have different shapes and dimensions. For example, the cross-section $C_1$ may have dimensions that are slightly larger than the dimensions of $C_2$.

The inner surface 212 may be hydrophobic or hydrophilic. Furthermore, the inner surface 212 of the interior contour 216 may have surface characteristics that facilitate controlling the flow of the liquid from the source well 130 to the reaction well 134. In a particular embodiment, the inner surface 212 has a common surface energy throughout the channel 174. However, in other embodiments, the inner surface 212 may have a surface energy gradient where one or more portions of the inner surface 212 are hydrophobic and one or more portions of the inner surface 212 are less hydrophobic. In other words, forces experienced by the liquid at the liquid-solid interface may change as the liquid flows down the channel 174. Likewise, the surface energy gradient may be formed by hydrophilic surfaces.

Figure 6A:
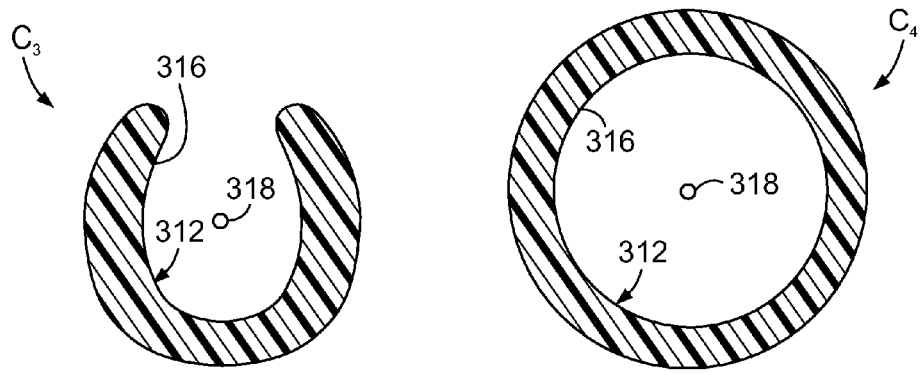
FIGS. 6A-C illustrate different pairs of cross-sections corresponding to microfluidic tubes formed in accordance with alternative embodiments.
Figure 6B:
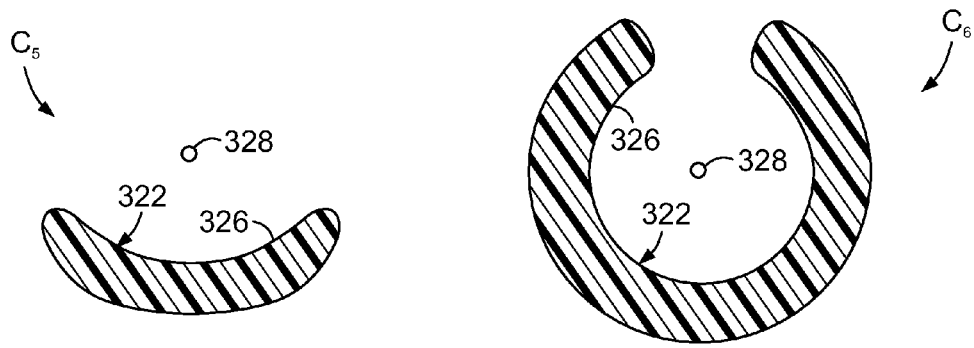
Figure 6C:
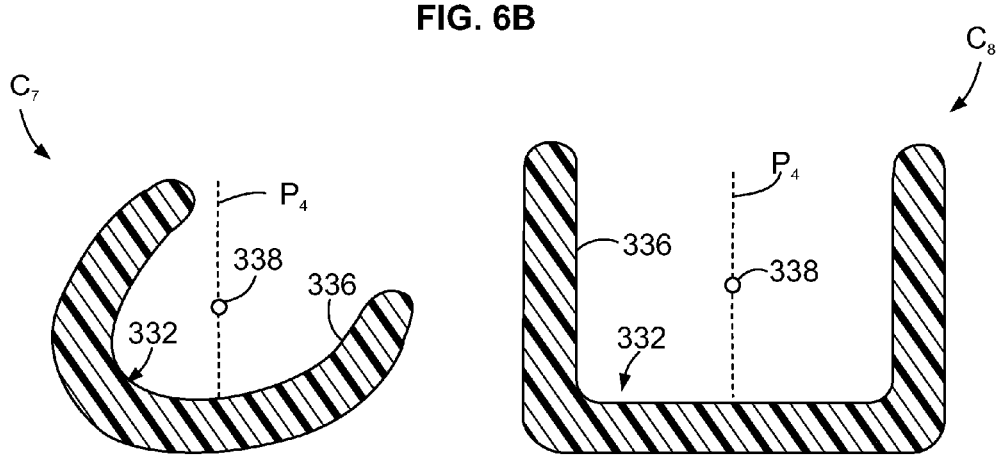

FIGS. 6A-6C illustrate pairs of cross-sections taken from corresponding microfluidic tubes (not shown) formed in accordance with alternative embodiments. More specifically, FIG. 6A shows cross-sections $C_3$ and $C_4$ taken from an outlet portion and an inlet portion, respectively, of a corresponding microfluidic tube. The cross-section $C_3$ is similar to the cross-section $C_1$ (FIG. 5). However, the cross-section $C_4$ has an interior contour 316 with an inner surface 312 that completely surrounds the longitudinal axis 318. For example, the interior contour 316 of the cross-section $C_4$ may be a circle, an oval, or another geometric shape.

FIG. 6B shows cross-sections $C_5$ and $C_6$ taken from an outlet portion and an inlet portion, respectively, of a corresponding microfluidic tube and show an interior contour 326. As shown, the cross-section $C_6$ is similar to the cross-section $C_2$ (FIG. 5). However, the cross-section $C_5$ is substantially open-faced. An inner surface 322 curves about a longitudinal axis 328, but does not surround or partially encircle the longitudinal axis 328. FIG. 6C shows cross-sections $C_7$ and $C_8$ taken from an outlet portion and an inlet portion, respectively, of a corresponding microfluidic tube and show an interior contour 336. Unlike the previous described cross-sections, the cross-section $C_7$ is not symmetrical about a plane $P_4$ extending through a longitudinal axis 338. Such cross-sections may be used when it is desired to deposit the liquid into a certain location within the reaction well (e.g., in a corner of the well or on a sidewall). Furthermore, an inner surface 332 of a cross-section is not required to curve about the corresponding longitudinal axis. For example, as shown in FIG. 6C, the cross-section $C_8$ has a rectangular-shaped interior contour 336 that surrounds the longitudinal axis 338.

In particular embodiments, the cross-sections $C_1$-$C_8$ described above with respect to FIGS. 5 and 6A-6C may be along any portion of the corresponding tube. Typically, at least a portion of the tube 144 will have a cross-section with a discontinuity section, such as the gap G (FIG. 4). Furthermore, a microfluidic tube may have a uniform cross-section throughout the length of the tube. In another embodiment, the tube 144 (FIG. 5) has a circular cross-section throughout the length $L_2$ (FIG. 5) of the tube 144 (i.e., the tube 144 is not open-sided).

Figure 7:
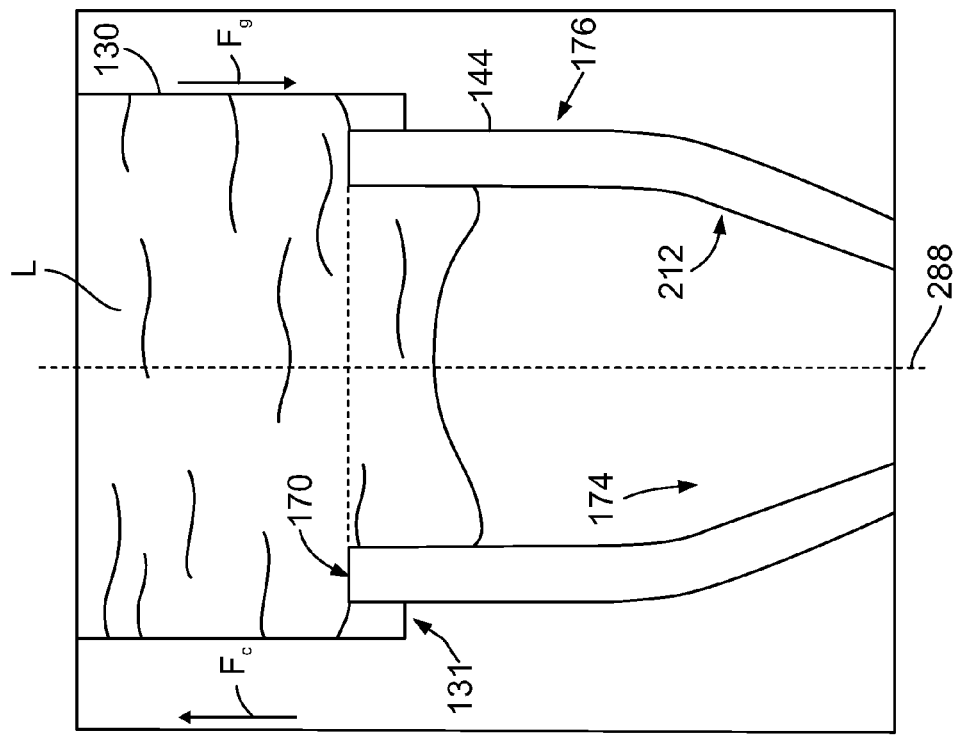
FIG. 7 illustrates the flow of liquid from a source well and into a channel of the tube shown in FIG. 3.

FIG. 7 illustrates the initial flow of a liquid L from the source well 130 into the channel 174 of the tube 144. To convey the liquid L through the channel 174, the tube 144 (and support structure) may be held in a dispensing orientation. In the dispensing orientation, the longitudinal axis 288 of the tube 144 is held with respect to the gravitational force direction $F_g$ such that the longitudinal axis 288 extends along the gravitational force direction $F_g$. In the illustrated embodiment, the longitudinal axis 288 and the gravitational force direction $F_g$ are substantially parallel. However, the longitudinal axis 288 is not required to extend parallel to the gravitational force direction $F_g$ when held in the dispensing orientation. For example, the longitudinal axis 288 may form an angle with respect to the gravitational force direction $F_g$ that allows gravity to draw or pull the liquid L through the channel 174. As an example, the longitudinal axis 288 may form an angle of 45 degrees or less with respect to the gravitational force direction $F_g$ when in the dispensing orientation.

When the microplate 122 (FIG. 2) is inverted, the cohesive and adhesive forces of the liquid L generate the capillary force $F_c$ that is greater than the gravitational force $F_g$. As such, the liquid L is prevented from draining out of the source well 130. To remove the liquid L, the inlet 170 of the tube 144 is inserted through the opening 131 of the source well 130. When the inlet 170 is advanced into source well 130, the liquid L is displaced by the inlet portion 176 of the tube 144. A portion of the liquid L may be forced into the channel 174 of the tube 144. Furthermore, the inner surface 212 of the channel 174 may interact with the liquid L through adhesive forces to facilitate drawing the liquid L from the source well 130. Upon contact of the liquid L by the inlet 170, cohesive forces holding the liquid L in the source well 130 may be reduced such that liquid L is drawn into the inlet 170. The gravitational force $F_g$ may also facilitate drawing the liquid L therein. As the liquid L is drawn into the channel 174, the cohesive forces of the liquid L may facilitate pulling the liquid L from the source well 130 and into the channel 174. When a substantial portion of the liquid L is within the channel 174, the gravitational force $F_g$ may continue to move the liquid L therethrough.

The dimensions of the tube 144 at the inlet portion 176 may be sized and shaped to control the flow of the liquid L therein. For example, the dimensions of the tube 144 may be configured based on the surface energy of the inner surface 212 and the surface tension of the liquid L. In one embodiment, the inner surface 212 is hydrophobic and the liquid L is an aqueous or polar liquid. Alternatively, the inner surface 212 may be hydrophilic and the liquid L may be non-polar. In other embodiments, at least a portion of the inner surface 212 is hydrophobic and the liquid L is a non-polar liquid or at least a portion of the inner surface 212 is hydrophilic and the liquid L is an aqueous or polar liquid.

Furthermore, the liquid L may be removed from the source well 130 passively and/or conveyed passively through the tube 144. In an alternative embodiment, the liquid L is actively removed from the source well using a pump. The dimensions of the tube 144 may be reconfigured based upon the pumping abilities of the pump.

Figure 8:
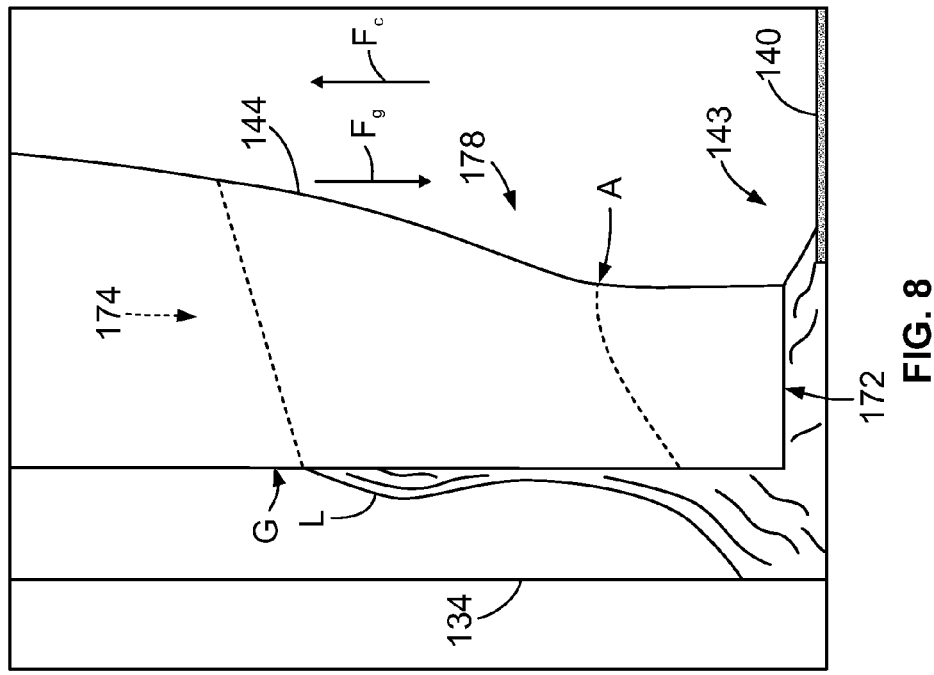
FIG. 8 is a side view of the flow of liquid from the channel of the tube shown in FIG. 3 and into a reaction well.

FIG. 8 is a side view of the tube 144 as the liquid L flows through the channel 174 and into the reaction well 134 of the microplate 124 (FIG. 2). In some embodiments, the outlet portion 178 of the tube 144 may be configured to reduce the flow of the liquid L as compared to the flow of the liquid L within the inlet portion 176 (FIG. 3). For example, the size and shape of the outlet portion 178 and/or the surface energy of the inner surface 212 (FIG. 4) within the outlet portion 178 may be configured to reduce the flow of the liquid L as the liquid L approaches a predetermined point along the tube 144 (indicated as point A). At point A, a sum of the forces experienced by the liquid L may result in stopping the flow of the liquid L toward the bottom 143. For example, a magnitude of the capillary forces $F_c$ may be greater than the gravitational force $F_g$ experienced by the liquid L. As such, a volume of the liquid L may gather within the channel 174 above point A. The gravitational force $F_g$ may cause the liquid L to flow out of the gap G. The liquid L may then flow into the reaction well 134. After a predetermined amount of time, a significant portion of the liquid L may be loaded or deposited into the reaction well 134.

FIG. 8 illustrates an example of one embodiment that passively controls the flow of the liquid L into the reaction well 134 where significant forces experienced by the liquid L are the capillary forces $F_c$ and the gravitational force $F_g$. However, in other embodiments, other forces may be involved in controlling the flow of the liquid L. For example, the tubes 144 may experience a centripetal force that causes the liquid L to flow downstream (i.e., from the inlet 170 toward the outlet 172) until the liquid L reaches the point A where the capillary forces $F_c$ prevent further movement. Also, the liquid L may be pumped (i.e., by being pushed or vacuumed through the system) until the liquid L reaches point A. In alternative embodiments, the liquid L may be drawn through the tube 144 by capillary forces $F_c$ and movement may be stopped by other forces (e.g., the gravitational force Fg, centripetal force, forces through pumping or vacuuming).

Furthermore, in other embodiments, the liquid L may flow through the channel 174 and out of the outlet 172. For example, the outlet portion 178 may be sized and shaped such that the liquid L is capable of flowing therethrough. Furthermore, the inner surface 212 (FIG. 4) of the tube 144 may be coated with a substance or the tube may be manufactured from a predetermined material such that the surface energy of the inner surface 212 along the outlet portion 178 reduces the capillary forces $F_c$ to allow the liquid L to flow through the outlet 172.

When the liquid L is loaded into the reaction well 134, the liquid L may cover the sample region 140. In one embodiment, the sample region 140 may comprise a chip having a chemical sample thereon. When the liquid L is fully loaded onto the bottom 143 of the reaction well 134, a bead formed by the liquid L may entirely cover a surface of the sample region. The volume of the liquid L that is ultimately transferred into the reaction well 134 can be controlled by selecting appropriate characteristics of the liquid L, such as a volume of the liquid L in source wells 130 before the transfer, and by selecting properties of the tube 144, such as volume capacity, tube shape, tube surface characteristics and other characteristics set forth herein. Alternatively or additionally, the volume of transferred liquid L can be controlled by the amount of time that the tubes 144 of the fluidic device 126 is in contact with the source wells 130 and/or reaction wells 134.

Figure 9:
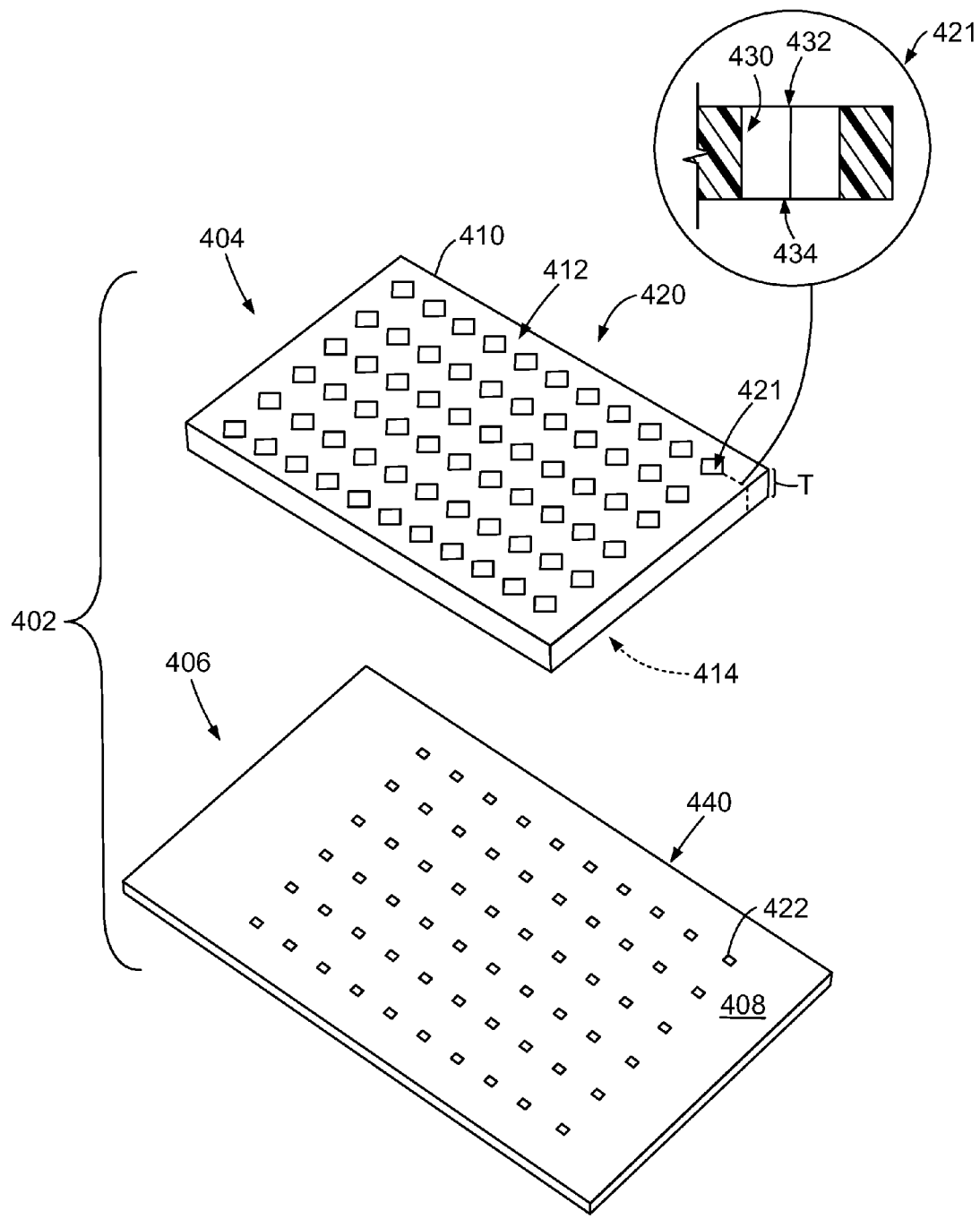
FIG. 9 is an exploded view of a microplate formed in accordance with one embodiment.

FIG. 9 is an exploded view of a microplate 402 that may be used, for example, with the fluidic system 120 described with reference to FIG. 2. The microplate 402 may be assembled from multiple components. In one embodiment, the microplate 402 includes a gasket 404 that is mounted onto a substrate 406 having a mounting surface 408. The gasket 404 has a body 410 that is configured to be mounted to the mounting surface 408. For example, the body 410 may have opposing sides 412 and 414 and a substantially uniform thickness T extending therebetween. The gasket 404 may include an array 420 of passages 421 that extend through the thickness T. Each passage 421 is defined by a wall surface 430 (shown in a cut-out portion) that extends through the body 410 from an open inlet 432 to an open outlet 434.

Also shown, the substrate 406 has a matching array 440 of sample regions 422. The sample regions 422 include biomolecules that are immobilized onto the mounting surface 408 of the substrate 406. The sample regions 422 may be immobilized on chips that are positioned on the mounting surface 408 or the sample regions 422 may be formed directly onto the mounting surface 408. Also, the mounting surface 408 may be substantially smooth and planar or, alternatively, may have cavities, recesses, indentations or the like.

To form the microplate 402, the gasket 404 is mounted onto the mounting surface 408 of the substrate. The passages 421 of the gasket 404 are aligned with corresponding sample regions 422 so that the sample regions 422 are exposed or are accessible through the corresponding passages 421. The gasket 404 and substrate 406 may be held tightly together such that an interface 415 (shown in FIG. 11) extends along the mounting surface 408 and the side 414. The interface 415 may be sealed so that liquid does not leak therethrough. In some embodiments, an adhesive may be placed on the side 414 and/or the mounting surface 408 in order to couple the gasket 404 to the mounting surface 408. Also, the gasket 404 and/or the substrate 406 may have mating features that engage each other and fasten the gasket 404 and substrate 406 together. For example, a post (not shown) projecting from the substrate 406 may form an interference fit with a corresponding cavity (not shown) in the gasket 404. Furthermore, other devices, such as tabs or a clamp, may be used to hold the gasket 404 onto the mounting surface 408.

In alternative embodiments, the microplate 402 may have a unitary body where the structural features of the gasket 404 and the substrate 406 are integrally formed. For example, the microplate may be a multi-well plate where one or more sample regions (e.g., a chip having a microarray thereon) are located in each well. In another alternative embodiment, the microplate or the gasket 404 may have the tubes 144 (FIG. 5) integrally formed with the microplate or the gasket 404. In such embodiments, a fluidic device, such as the fluidic device 126 in FIG. 3, is not required.

Figure 10:
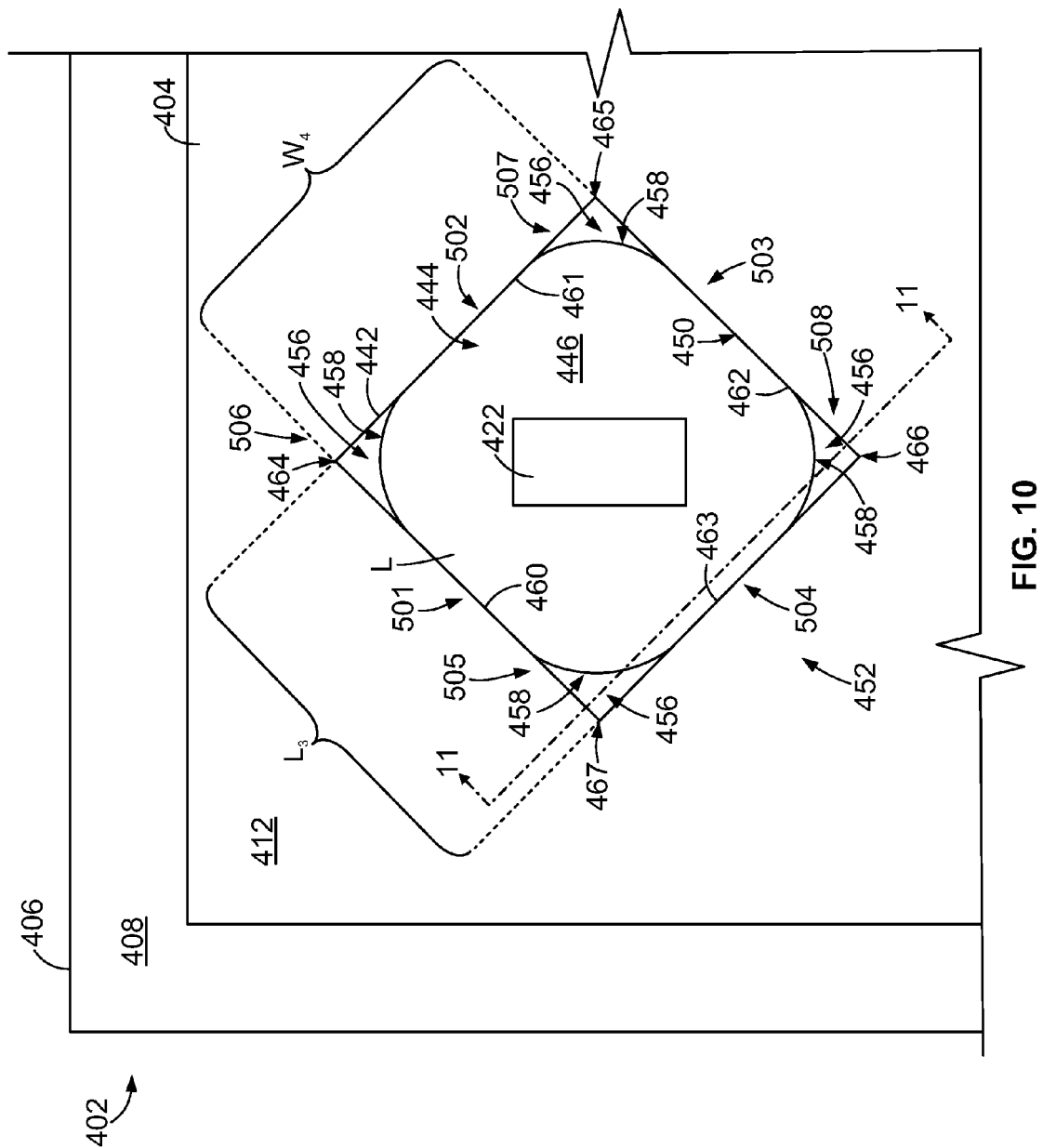
FIG. 10 is a top-plan view of a portion of the microplate shown in FIG. 9.

FIG. 10 is a top plan view of a portion of the microplate 402. When the gasket 404 is mounted onto the mounting surface 408 of the substrate 406, the passages 421 (FIG. 9) are closed off by the mounting surface 408 thereby forming a well 442 having an open inlet 444, a closed end 446, and a cavity 448 (FIG. 11) extending therebetween. The cavity 448 is defined by a wall surface 450 that may form a plurality of sidewalls 460-463. The wall surface 450 may also form a plurality of corners 464-467 that join the sidewalls 460-463. As shown in FIG. 10, the wall surface 450 has a cross-sectional contour 452 that may be sized and shaped for containing an approximate amount of the liquid L. Also shown, the well 442 has the sample region 422 located at the closed end 446. The sample region 422 may be centered within the well 442 or may be positioned nearer to one of the sidewalls 460-463.

The cross-sectional contour 452 may be sized and shaped to facilitate removing gases or microbubbles from a confined space that a liquid L enters. More specifically, when the liquid L at least partially fills the well 442, the cross-sectional contour 452 is shaped to define a spacing 456 between the wall surface 450 and a liquid surface 458. The spacing 456 may extend along one or more of the corners 464-467 and is configured to provide a gas exhaust path EP (shown in FIG. 11) to permit discharge of gas from a well 442 that a liquid L enters.

The cross-sectional contour 452 may be rectangular-shaped and have a length $L_3$ and a width $W_4$. In some embodiments, the cross-sectional contour 452 has at least one dimension that is smaller than a dimension that the drop of liquid L would have been but for the cross-sectional contour 452 of the wall surface 450. For example, in accordance with some embodiments, the cross-sectional contour 452 has a dimension (e.g., the length $L_3$ or the width $W_4$) that is less than the resting diameter $D_R$ (FIG. 1) of the amount of liquid L deposited into the well 442. In other words, the cross-sectional contour 452 has a dimension that is less than a diameter of the amount of liquid L when it is deposited onto a flat surface and is not contained by walls. Nevertheless, as set forth herein, an exhaust path EP (FIG. 11) can be present while the liquid L occupies the well 442 defined by the cross-sectional contour 452. In a particular embodiment, the cross-sectional contour 452 is substantially rectangular or square-shaped and the length $L_3$ and the width $W_4$ are both less than the resting diameter $D_R$ of the amount of liquid L deposited into the well. Furthermore, in some embodiments, an area of a circle having the resting diameter $D_R$ for the amount of liquid L deposited into the well 452 is greater than an area of the cross-sectional contour 452.

Also, the cross-sectional contour 452 may be sized and shaped to include at least one continuous section, such as continuous sections 501-504, and at least one discontinuity section, such as discontinuity sections 505-508, when the liquid L has at least partially filled the well 442. As used herein, a "continuous section" includes that section of the cross-sectional contour that contacts the liquid L when a threshold amount of the liquid L has been deposited within the well 442. A "discontinuity section," as used herein, includes that section of the cross-sectional contour that does not contact the liquid L when a threshold amount has been deposited within the well 442. A threshold amount of the liquid L is an amount of the liquid L where the resting diameter $D_R$ of that amount of liquid L is greater than a dimension of the cross-sectional contour of the well.

The discontinuity sections 505-508 are shaped to provide the corresponding spacing 456 between the surface 458 of the liquid L and the wall surface 450 that extends from the closed end 446 of the well 442 toward the open inlet 444. In some embodiments, the cross-sectional contour 452 defines a non-circular contour. The discontinuity sections of the wall surface 450 include corresponding corners 464-467.

Figure 11:
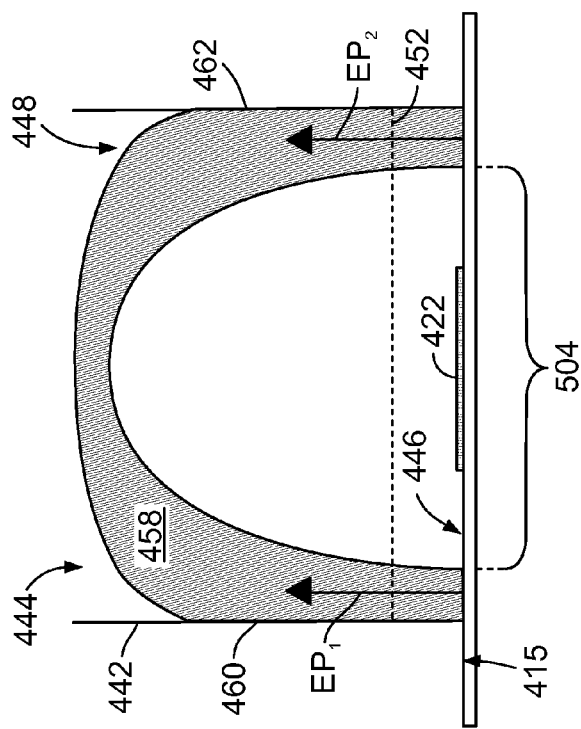
FIG. 11 is a cross-sectional view of a reaction well taken along a line 11-11 in FIG. 10.
Figure 12B:
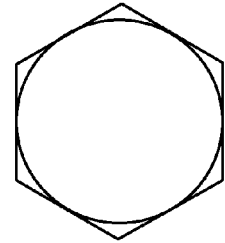
Figure 12A:
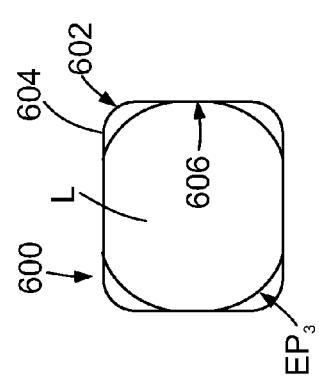

FIG. 11 is a cross-sectional view of the well 442 taken along the line 12-12 in FIG. 10. As shown, the gas exhaust paths $EP_1$ and $EP_2$ are defined by the sidewalls 460, 462, and 463 (FIG. 10) and the liquid surface 458. For example, the gas exhaust path $EP_1$ is defined by the sidewalls 460 and 463 and the liquid surface 458 and a surface of the closed end 446. Both gas exhaust paths $EP_1$ and $EP_2$ extend from the surface of the closed end 446 toward the open inlet 444. As shown, the closed end 446 has a substantially planar surface. However, in other embodiments, the closed end 446 may have a slightly curved surface or may have a slight depression.

As shown in FIG. 11, the well 442 has a height $H_3$ and the liquid L has a height $H_4$. When the liquid L is loaded into the well 442, the liquid L may fill a majority of a volume of the well 442 such that the continuous section 504 of the cross-sectional contour 452 is in contact with the liquid L. For example, the height $H_4$ reached by the liquid L within the well 442 may be substantially equal to the height $H_3$ while the well 442 maintains the gas exhaust paths $EP_1$ and $EP_2$ therein. Also, although the gas exhaust paths $EP_1$ and $EP_2$ extend from the surface of the closed end 446, alternative embodiments may include gas exhaust paths that extend along less than the height $H_3$ or $H_4$. More specifically, the liquid L may cover the surface of the closed end 446 up to where the corners 464-467 (FIG. 10) meet the closed end 446. In such embodiments, the gas exhaust paths may extend along a majority of the height $H_4$ of the liquid L within the well 442. For example, when the height $H_4$ is substantially equal to the height $H_3$, the gas exhaust paths may extend at least ¾ of the height $H_3$.

In order to determine the locations of the continuous sections 501-504 (FIG. 10) and discontinuity sections 505-508 (FIG. 10), the dimensions and shape of the cross-sectional contour 452 may be configured based upon a surface energy of the wall surface 450 and the surface tension of the liquid L. In one example, the wall surface 450 may be hydrophobic and the liquid L may be aqueous or polar. Alternatively, the wall surface 450 may be hydrophilic and the liquid L may be non-polar.

Furthermore, the composition of the surrounding gases (e.g., ambient air) and a range in temperatures experienced by the liquid L during the biological or chemical assay may also be considered. As such, the cross-sectional contour 452 may be shaped to maintain the gas exhaust path EP through a range of temperatures. For example, the gas exhaust path EP may exist within the well 442 at an ambient temperature (e.g., 70° F.) when the liquid L is first loaded and also exist during a thermal cycle where the temperature is changed, such as between 0° F. and 400° F. In particular applications, the temperature can be between 75° F. and 150° F. For example, the methods and devices described herein can be used for hybridization processes carried at temperatures below about 90° F. or more preferably below about 75° F. The methods and devices can be used at temperatures where nucleic acids are denatured, such as at temperatures greater than 100° F. In particular embodiments, the methods and devices can be used in a humidified environment to reduce evaporation of liquids or under inert gas atmosphere to reduce oxidation and other reactions that would otherwise occur in the presence of air. Accordingly, the size or shape of the spacing 456 and gas exhaust path EP may be affected by the temperature change. For example, the liquid surface 458 may expand closer to the wall surface 450 when the temperature increases. However, the gas exhaust path EP may still exist between the closed end 446 and the open inlet 444 during the temperature change.

In one embodiment, an amount of the liquid L loaded into the well 442 is significantly more than an amount of liquid L necessary to completely cover the sample region 422 or the closed end 446. For example, the amount of liquid L loaded into the well 442 may be based upon an amount of liquid L that will evaporate after experiencing a thermal cycle.

FIGS. 12A-12E illustrate cross-sectional contours of wells (not shown) formed in accordance with alternative embodiments. The cross-sectional contours of the wells may have various shapes that deviate from the natural shape of the liquid L when it is deposited onto a planar surface. As shown in 12A, a cross-sectional contour 600 may include at least one discontinuity section 602 formed by a rounded corner 604 in the wall surface 606. A gas exhaust path $EP_3$ may be defined between the rounded corner 604 and a surface of the liquid L. Furthermore, the cross-sectional contour may have a polygonal shape, such as a hexagon shown in FIG. 12B. Also, the cross-sectional contour may also be shaped as a triangle, a parallelogram (e.g., diamond-shaped), and a pentagon.

Figure 12D:
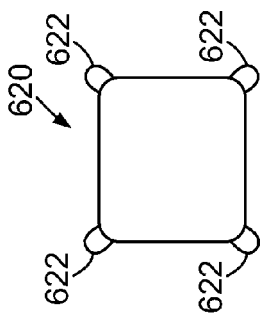
FIGS. 12A-F illustrate cross-sectional contours of wells that may be used with a microplate formed in accordance with alternative embodiments.
Figure 12F:
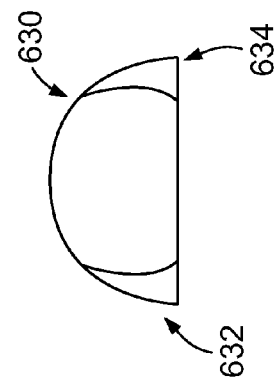
Figure 12C:
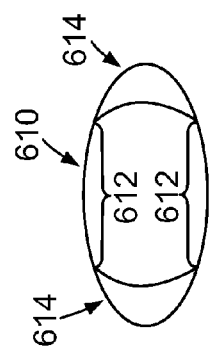

FIG. 12C illustrates a cross-sectional contour 610 having an elongated oval shape. The cross-sectional contour 610 may include continuous sections 612 along shorter dimensions of the cross-sectional contour 610, but may include discontinuity sections 614 along the longer dimensions. FIG. 12F illustrates a cross-sectional contour 630 having a semi-circle shape. The discontinuity sections may be formed at corners 632 and 634.

Figure 12E:
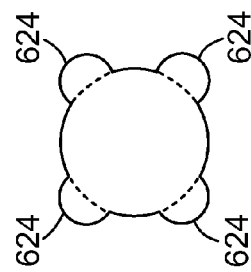

FIGS. 12D and 12E include pocket projections 622 and 624, respectively. In FIG. 12D, a cross-sectional contour 620 has a substantially square-like shape. However, the pocket projections 622 project outward from where corners should be located. In FIG. 12E, a cross-sectional contour 623 has a substantially circular shape. However, the pocket projections 624 project outward therefrom. As shown, continuous sections of the cross-sectional contour 623 have a first radius of curvature and discontinuity sections formed by the pocket projections 624 have a second radius of curvature that is less than the first radius of curvature. Accordingly, embodiments described herein include wells having cross-sectional contours configured to facilitate venting gases from the well into which the liquid is deposited. The shapes of the cross-sectional contours may be configured to conserve space or allow the wells to be positioned closely to one another.

Figure 13:
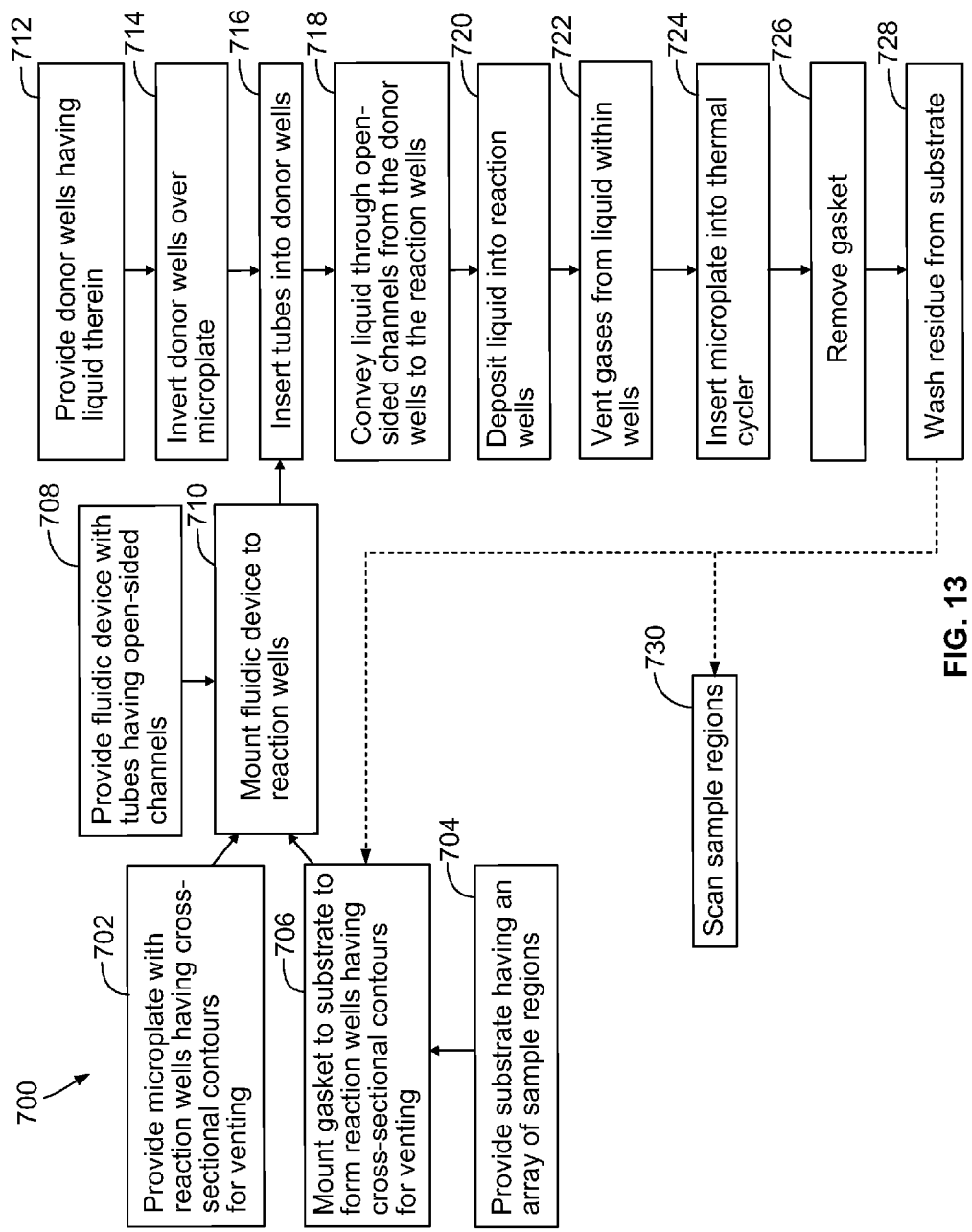
FIG. 13 is a flowchart of a method in accordance with one embodiment.

FIG. 13 is a block diagram illustrating a method 700 for performing a multiplex assay. The method 700 may use the fluidic devices and systems described above. First, a microplate may be provided that includes reaction wells having cross-sectional contours as described above for venting gases from a confined space that the liquid enters. The reaction wells may include sample regions therein. For example, the microplate may be a pre-manufactured multi-well plate at 702. Alternatively, a substrate may be provided at 704 having an array of sample regions thereon. A gasket may then be mounted to the substrate at 706 so that the reaction wells having the cross-sectional contours are formed. A fluidic device having an array of tubes with open-sided channels is provided at 708 and mounted to the microplate at 710 such that portions of the tubes are located within corresponding reaction wells.

At 712, a microplate having an array of donor wells may be provided and inverted at 714. The donor wells include a liquid or a solution of target molecules that have a binding affinity for certain probes on microarrays of the sample regions. The target molecules may be labeled so that the target molecules are optically detectable (e.g., through fluorescence). The tubes of the fluidic device may be inserted into corresponding donor wells at 716 such that the tubes are held in a dispensing orientation. As each tube is inserted into the donor well, the tube displaces the liquid within the donor well thereby forcing the liquid into the open-sided channel of the tube. The adhesive and cohesive forces and the gravitational force draw the liquid from the donor well.

The liquid flows through the open-sided channel of the tube and is conveyed at 718 from the donor well and deposited or loaded into the corresponding reaction well at 720. As the liquid enters each reaction well and flows toward the sample region, the liquid at least partially fills the reaction well. The liquid may flow along a continuous section of the wall surface and remain separated from a discontinuity section of the wall surface. The separation forms a spacing and maintains a gas exhaust path to permit discharge of gas (i.e., vent) from the closed end of the well at 722.

The microplate may be inserted into a thermal cycler (e.g., oven) at 724 where the microplate is heated to a desired temperature for a predetermined period of time. When the microplate is removed from the thermal cycler, the gasket may be removed at 726 from the substrate. The substrate may then be washed at 728 to remove any undesired residue. The sample regions may then be scanned by a detector at 730 to detect any optically detectable characteristics of the microarray. For example, the substrate may be scanned to detect a fluorescence level of the probes on the microarray.

Alternatively, after the residue has been washed from the substrate at 728, the substrate may be mounted by another gasket so that other fluids may be added to the substrate and processed through another thermal cycle for reacting with the probes of the sample regions.

Although the above described embodiments illustrate the gravitational force $F_g$ being significant in controlling the flow of the liquid L through the tube 144 and also while the liquid L rests within the well 442, other forces may be applied to the fluidic system that are ultimately stronger than the gravitational force $F_g$ or work in conjunction with the gravitational force $F_g$. For example, the liquid L may experience pumping or centripetal force through the tube 144 or while within the well 442. Furthermore, the surrounding environment (e.g., temperature, composition of the ambient air, pressure of the ambient air) may be changed to affect the liquid L in a desired or predetermined manner.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the specific components and processes described herein are intended to define the parameters of the various embodiments of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

What is claimed is:

1. A method for venting a well receiving a liquid, the method comprising:
   providing a microplate including a well having a cavity with an open inlet and a closed end, the cavity extending between the open inlet and the closed end, the cavity being defined by a wall surface that has a cross-sectional contour that includes at least one continuous section and at least one discontinuity section; and
   depositing a liquid into the open inlet of the well, the liquid entering the cavity and flowing toward the closed end to at least partially fill the well, the liquid flowing along the continuous section of the wall surface and remaining separated from the discontinuity section of the wall surface thereby maintaining a gas exhaust path along a spacing between the liquid and the discontinuity section as the liquid flows toward the closed end to permit discharge of gas from the closed end of the well.

2. The method in accordance with claim 1 wherein the wall surface of the well is hydrophobic and the liquid is polar or aqueous.

3. The method in accordance with claim 1 wherein the wall surface of the well is hydrophilic and the liquid is non-polar.

4. The method in accordance with claim 1 wherein the cross-sectional contour defines a non-circular contour.

5. The method in accordance with claim 1 wherein the wall surface has a surface energy and the liquid has a surface tension, the cross-sectional contour of the cavity being shaped based on the surface energy and the surface tension to provide the spacing between the liquid and the discontinuity section of the wall surface.

6. The method in accordance with claim 1 wherein providing the microplate includes mounting a gasket onto a substrate having a mounting surface, the gasket including a passage, the well being formed by the mounting surface of the substrate and the passage when the gasket is mounted onto the substrate.

7. The method in accordance with claim 1 further comprising agitating the microplate to facilitate venting bubbles into the gas exhaust path.

8. The method in accordance with claim 1 wherein the cross-sectional contour is shaped substantially like one of a triangle, a parallelogram, a pentagon, and a hexagon.

9. The method in accordance with claim 1 wherein the discontinuity section includes a corner formed in the wall surface, the gas exhaust path being defined by the corner and the liquid.

10. The method in accordance with claim 1 wherein the discontinuity section includes a rounded corner formed in the wall surface, the gas exhaust path being defined by the rounded corner and the liquid.

11. The method in accordance with claim 1 wherein the continuous section has a first radius of curvature and the discontinuity section has a second radius of curvature.

12. The method in accordance with claim 1 wherein the gas exhaust path extends from the closed end to the inlet.

13. The method in accordance with claim 1 wherein the closed end comprises a microarray and the liquid comprises at least one target molecule that binds to the microarray.

14. The method in accordance with claim 13 further comprising detecting binding of the at least one target molecule to the microarray.

15. The method in accordance with claim 14 wherein the microplate includes a gasket mounted onto a substrate having a mounting surface, the gasket including a passage, the well being formed by the mounting surface of the substrate and the passage when the gasket is mounted onto the substrate.

16. The method in accordance with claim 15 wherein the gasket is removed prior to said detecting.

17. The method in accordance with claim 1 wherein the closed end comprises a sample region and the liquid comprises at least one biomolecule that binds to the sample region.

18. The method in accordance with claim 17 wherein the wall surface of the well is hydrophobic and the liquid is polar or aqueous.

19. The method in accordance with claim 17 wherein the wall surface of the well is hydrophilic and the liquid is non-polar.

20. The method in accordance with claim 17 wherein the cross-sectional contour defines a non-circular contour.

21. The method in accordance with claim 17 wherein the wall surface has a surface energy and the liquid has a surface tension, the cross-sectional contour of the cavity being shaped based on the surface energy and the surface tension to provide the spacing between the liquid and the discontinuity section of the wall surface.

22. The method in accordance with claim 17 wherein providing the microplate includes mounting a gasket onto a substrate having a mounting surface, the gasket including a passage, the well being formed by the mounting surface of the substrate and the passage when the gasket is mounted onto the substrate.

23. The method in accordance with claim 17 further comprising agitating the microplate to facilitate venting bubbles into the gas exhaust path.

24. The method in accordance with claim 17 wherein the cross-sectional contour is shaped substantially like one of a triangle, a parallelogram, a pentagon, and a hexagon.

25. The method in accordance with claim 17 wherein the discontinuity section includes a corner formed in the wall surface, the gas exhaust path being defined by the corner and the liquid.

26. The method in accordance with claim 17 wherein the discontinuity section includes a rounded corner formed in the wall surface, the gas exhaust path being defined by the rounded corner and the liquid.

27. The method in accordance with claim 17 wherein the continuous section has a first radius of curvature and the discontinuity section has a second radius of curvature.

28. The method in accordance with claim 17 wherein the gas exhaust path extends from the closed end to the inlet.

* * * * *